(12) United States Patent
Lintereur et al.

(10) Patent No.: US 10,980,942 B2
(45) Date of Patent: Apr. 20, 2021

(54) INFUSION DEVICES AND RELATED MEAL BOLUS ADJUSTMENT METHODS

(71) Applicant: MEDTRONIC MINIMED, INC., Northridge, CA (US)

(72) Inventors: Louis J. Lintereur, Stevenson Ranch, CA (US); Anirban Roy, Agoura Hills, CA (US); Benyamin Grosman, Valley Village, CA (US); Patrick E. Weydt, Moorpark, CA (US); Neha J. Parikh, West Hills, CA (US); Di Wu, Glendale, CA (US); Ali Dianaty, Porter Ranch, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 144 days.

(21) Appl. No.: 16/275,289

(22) Filed: Feb. 13, 2019

(65) Prior Publication Data
US 2020/0101221 A1 Apr. 2, 2020

Related U.S. Application Data

(60) Provisional application No. 62/739,017, filed on Sep. 28, 2018.

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC . A61B 5/14532; A61B 5/4848; A61B 5/4866; A61M 2005/14208;
(Continued)

(56) References Cited

U.S. PATENT DOCUMENTS 4,562,751 A 1/1986 Nason et al.
4,685,903 A 8/1987 Cable et al.
(Continued)

OTHER PUBLICATIONS

International Search Report and Written Opinion of International Application No. PCT/US2019/035636, dated Aug. 22, 2019, 13 pp.

*Primary Examiner* — Deanna K Hall
(74) *Attorney, Agent, or Firm* — Shumaker & Sieffert, P.A.

(57) ABSTRACT

Medical devices and related systems and operating methods are provided. A method of operating an infusion device capable of delivering fluid influencing a physiological condition to a patient involves obtaining an event indication, such as a meal indication, determining an initial bolus amount based on the event indication, and determining predicted values for the physiological condition of the patient during a time window into the future based at least in part on the initial bolus amount. When the predicted values violate a threshold during the time window, the control system identifies an adjusted bolus amount that results in the predicted values for the physiological condition satisfying the threshold during the time window from within a search space defined by the initial bolus amount and operates an actuation arrangement of the infusion device to deliver the adjusted bolus amount of the fluid to the patient.

15 Claims, 11 Drawing Sheets

(51) Int. Cl.
  *G16H 20/17* (2018.01)
  *G16H 50/20* (2018.01)
  *A61B 5/145* (2006.01)

(52) U.S. Cl.
  CPC .......... *A61B 5/4866* (2013.01); *A61B 5/7275* (2013.01); *G16H 20/17* (2018.01); *G16H 50/20* (2018.01); *A61M 2205/3303* (2013.01); *A61M 2205/52* (2013.01); *A61M 2230/201* (2013.01)

(58) Field of Classification Search
  CPC ...... A61M 2205/3303; A61M 2205/50; A61M 2205/52; A61M 2230/201; A61M 5/14244; A61M 5/1723
  See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 2004/0193025 A1 | 9/2004 | Steil et al. |
| 2007/0123819 A1 | 5/2007 | Mernoe et al. |
| 2010/0160861 A1 | 6/2010 | Causey, III et al. |
| 2014/0066889 A1 | 3/2014 | Grosman et al. |
| 2015/0165117 A1 | 6/2015 | Palerm et al. |
| 2016/0279336 A1 | 9/2016 | Roy |

INFUSION DEVICES AND RELATED MEAL BOLUS ADJUSTMENT METHODS

CROSS-REFERENCE TO RELATED APPLICATION(S)

This application claims the benefit of U.S. provisional patent application Ser. No. 62/739,017, filed Sep. 28, 2018, the entire content of which is incorporated by reference herein.

TECHNICAL FIELD

Embodiments of the subject matter described herein relate generally to medical devices, and more particularly, embodiments of the subject matter relate to proactive bolus adjustments using physiological modeling.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a patient via a fluid path created between the reservoir and the body of a patient. Use of infusion pump therapy has been increasing, especially for delivering insulin for diabetics.

Control schemes have been developed to allow insulin infusion pumps to monitor and regulate a patient's blood glucose level in a substantially continuous and autonomous manner. Managing a diabetic's blood glucose level is complicated by variations in a patient's daily activities (e.g., exercise, carbohydrate consumption, and the like) in addition to variations in the patient's individual insulin response and potentially other factors. Some control schemes may attempt to proactively account for daily activities to minimize glucose excursions. At the same time, patients may manually initiate delivery of insulin prior to or contemporaneously with consuming a meal (e.g., a meal bolus or correction bolus) to prevent spikes or swings in the patient's blood glucose level that could otherwise result from the impending consumption of carbohydrates and the response time of the control scheme. That said, a manually-initiated bolus could introduce a risk of a postprandial glucose excursion if preceding insulin deliveries are not accounted for. Accordingly, there is a need to improve the efficacy of manual boluses and minimize postprandial glucose excursions.

BRIEF SUMMARY

Medical devices and related systems and operating methods are provided. An embodiment of a method of operating an infusion device capable of delivering fluid influencing a physiological condition to a patient involves a control system associated with the infusion device obtaining an event indication, determining an initial bolus amount based on the event indication, and determining predicted values for the physiological condition of the patient during a time window into the future based at least in part on the initial bolus amount. When the predicted values violate a threshold during the time window, the control system identifies an adjusted bolus amount that results in the predicted values for the physiological condition satisfying the threshold during the time window from within a search space defined by the initial bolus amount and operates an actuation arrangement of the infusion device to deliver the adjusted bolus amount of the fluid to the patient.

Another embodiment of method of operating an infusion device to deliver insulin to a patient in response to a meal indication involves obtaining glucose measurement data for the patient, obtaining historical insulin delivery data for the patient, determining an initial bolus amount based on an amount of carbohydrates corresponding to the meal indication, and determining an initial condition for the patient based at least in part on the glucose measurement data, the historical insulin delivery data, the initial bolus amount, and the amount of carbohydrates. The method continues by determining future insulin delivery data for the patient and determining predicted values for a glucose level of the patient during a postprandial time window based at least in part on the initial condition for the patient and the future insulin delivery data. When one or more of the predicted values for the glucose level fall below a threshold during the postprandial time window, the method continues by progressively reducing a search space defined by the initial bolus amount to identify an adjusted bolus amount that results in the predicted values for the glucose level satisfying the threshold during the postprandial time window based at least in part on the future insulin delivery data and an adjusted initial condition for the patient determined based at least in part on the glucose measurement data, the historical insulin delivery data, the adjusted bolus amount, and the amount of carbohydrates, and operating an actuation arrangement of the infusion device to deliver the adjusted bolus amount of the insulin to the patient.

An embodiment of an infusion system is also provided. The infusion system includes an actuation arrangement operable to deliver fluid capable of influencing a physiological condition to a patient, a user interface to receive input indicative of a meal for the patient, a sensing arrangement to obtain measurement data indicative of the physiological condition of the patient, a data storage element to maintain historical delivery data for the patient, and a control system coupled to the actuation arrangement, the sensing arrangement, the data storage element and the user interface to determine an initial bolus amount of the fluid based on the meal, and determine predicted values for the physiological condition of the patient during a time window into the future based at least in part on the initial bolus amount, the measurement data, the historical delivery data, and future delivery data. When the predicted values violate a threshold during the time window, the control system identifies an adjusted bolus amount within a search space defined by the initial bolus amount that results in updated predicted values for the physiological condition based at least in part on the adjusted bolus amount, the measurement data, the historical delivery data, and the future delivery data satisfying the threshold during the time window, and thereafter operates the actuation arrangement to deliver the adjusted bolus amount of the fluid to the patient This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
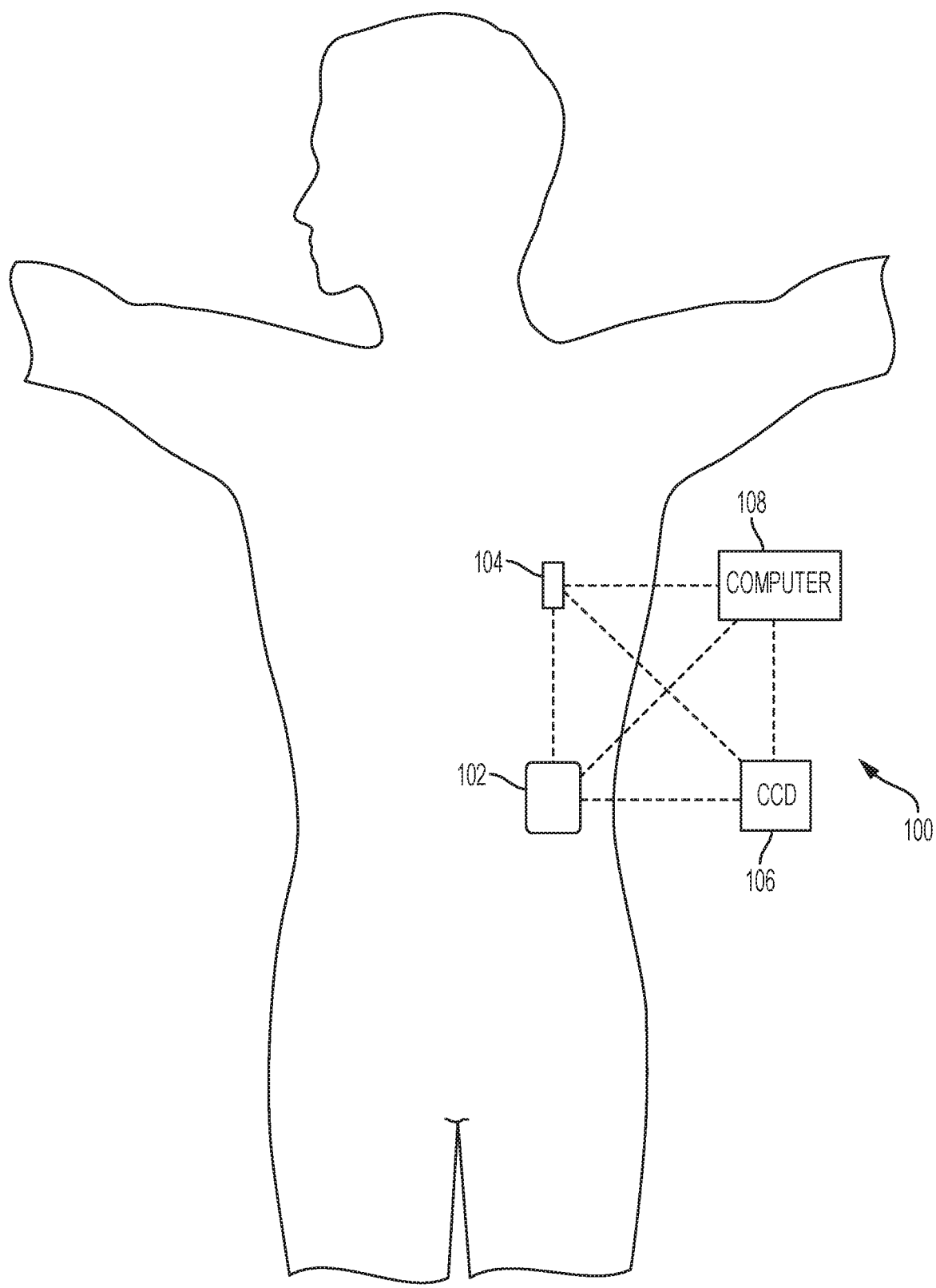
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter may be implemented in an equivalent manner in the context of other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. That said, the subject matter described herein can be utilized more generally in the context of overall diabetes management or other physiological conditions independent of or without the use of an infusion device or other medical device (e.g., when oral medication is utilized), and the subject matter described herein is not limited to any particular type of medication.

Generally, a fluid infusion device includes a motor or other actuation arrangement that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments of the subject matter described herein generally relate to proactively adjusting bolus amounts to account for automated or autonomous deliveries that precede administration of the bolus. As described in greater detail below in the context of FIGS. 9-11, in exemplary embodiments, one or more mathematical models for the patient's physiological response are utilized to predict or forecast future glucose levels for a patient based on the patient's current and/or recent glucose measurements and preceding insulin deliveries given a manually-input carbohydrate amount and corresponding initial meal bolus amount. In this regard, the initial meal bolus amount may be determined based on the manually-input carbohydrate amount and a carbohydrate ratio for the patient. When the patient's predicted future glucose level using the initial meal bolus amount is below a threshold value within a postprandial time window, the initial meal bolus amount is reduced to an amount that results in the patient's predicted future glucose level being maintained above threshold value throughout the postprandial time window. In exemplary embodiments, a golden ratio-based search or a Fibonacci search is utilized to progressively or iteratively reduce the search space defined by the initial meal bolus amount using intermediate values within the search space that progressively converge toward an adjusted bolus amount that is selected to be administered in lieu of the initial meal bolus amount. In this regard, in exemplary embodiments, the search attempts to maximize the maximum bolus dosage within the search space defined by the initial meal bolus amount while maintaining a predicted future glucose level for the patient that satisfies a postprandial hypoglycemic threshold during a predefined postprandial analysis time period.

By virtue of the physiological model for the patient's predicted future glucose level accounting for the preceding automated or autonomous insulin deliveries along with the patient's current glucose level and the current trend in the patient's glucose level, the adjusted bolus amount reduces the risk of a postprandial hypoglycemic event which could otherwise result from failing to account for automated or autonomous insulin deliveries or misestimating the amount of carbohydrates and/or the carbohydrate ratio. For example, in some embodiments, closed-loop control information may be automatically adjusted in advance of an anticipated event likely to influence the patient's glucose levels or insulin response. In this regard, prospective closed-loop control adjustments account for the relatively slow action of long-acting subcutaneously administered insulin by adjusting insulin delivery in advance of an event to increase or decrease the amount of yet to be metabolized insulin on board prior to start of the event. Thus, the adjusted bolus amount accounts for prospective closed-loop insulin deliveries in a manner that reduces the risk of a postprandial glucose excursion.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
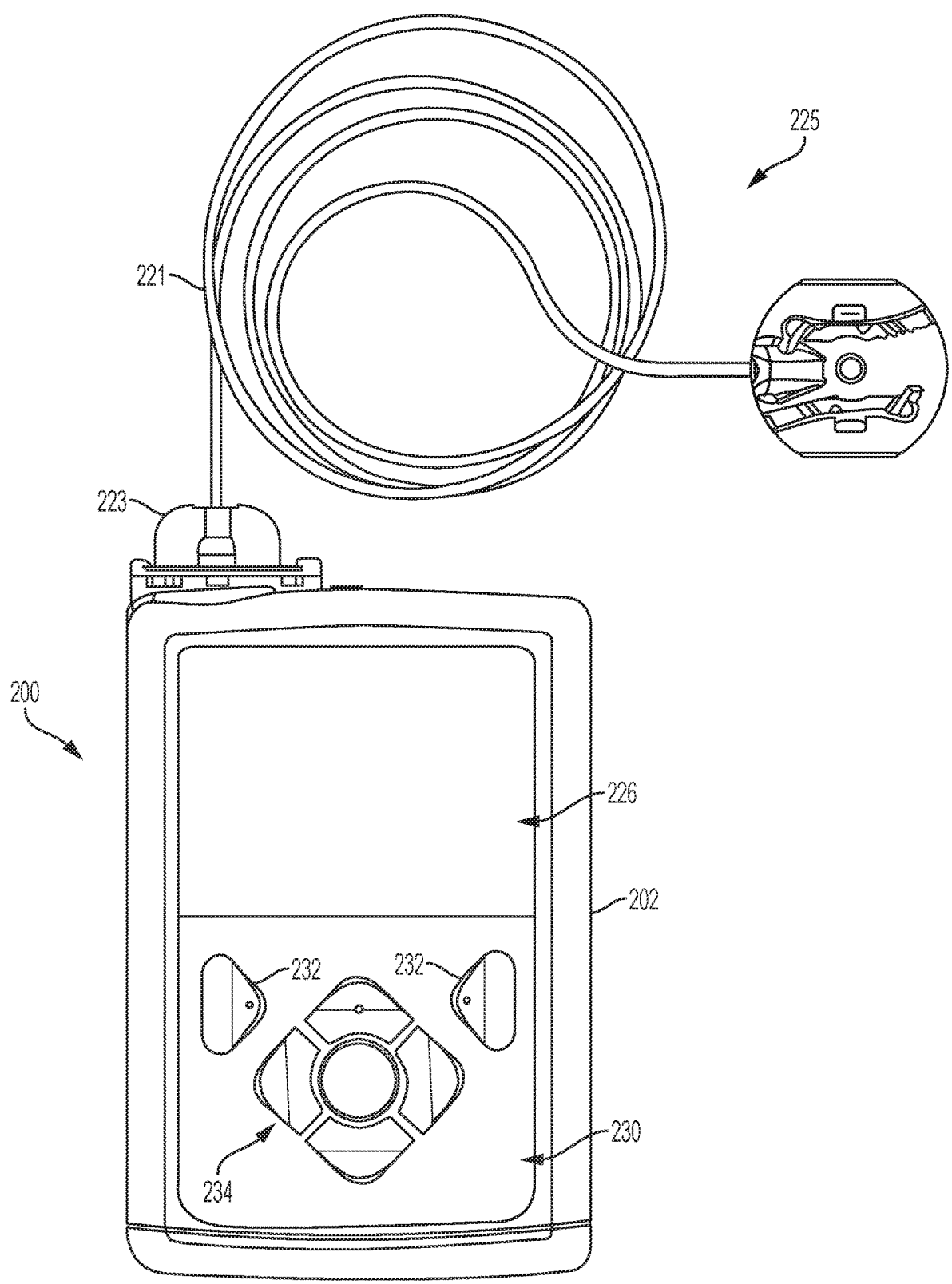
FIG. 2 depicts a plan view of an exemplary embodiment of a fluid infusion device suitable for use in the infusion system of FIG. 1.
Figure 3:
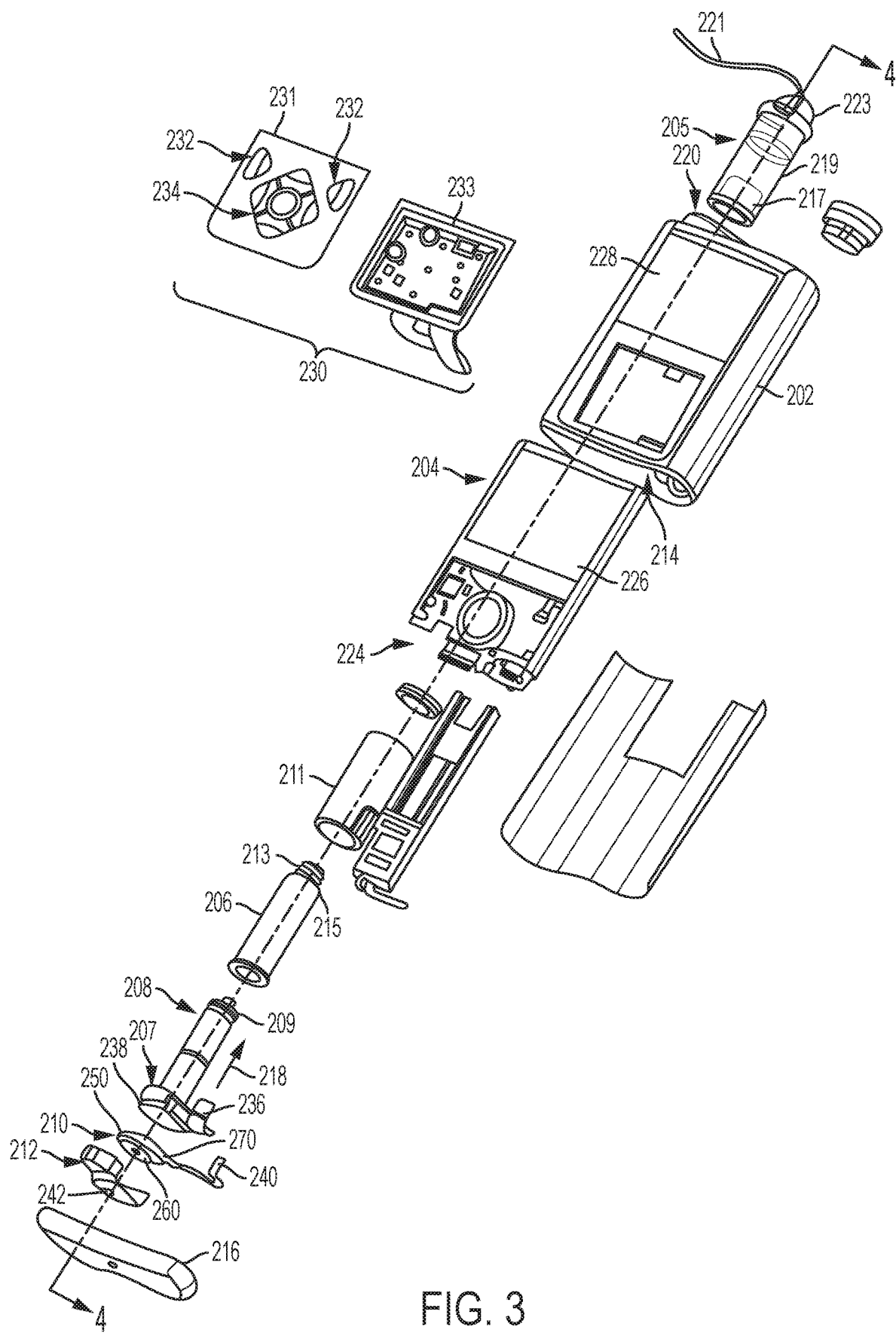
FIG. 3 is an exploded perspective view of the fluid infusion device of FIG. 2.
Figure 4:
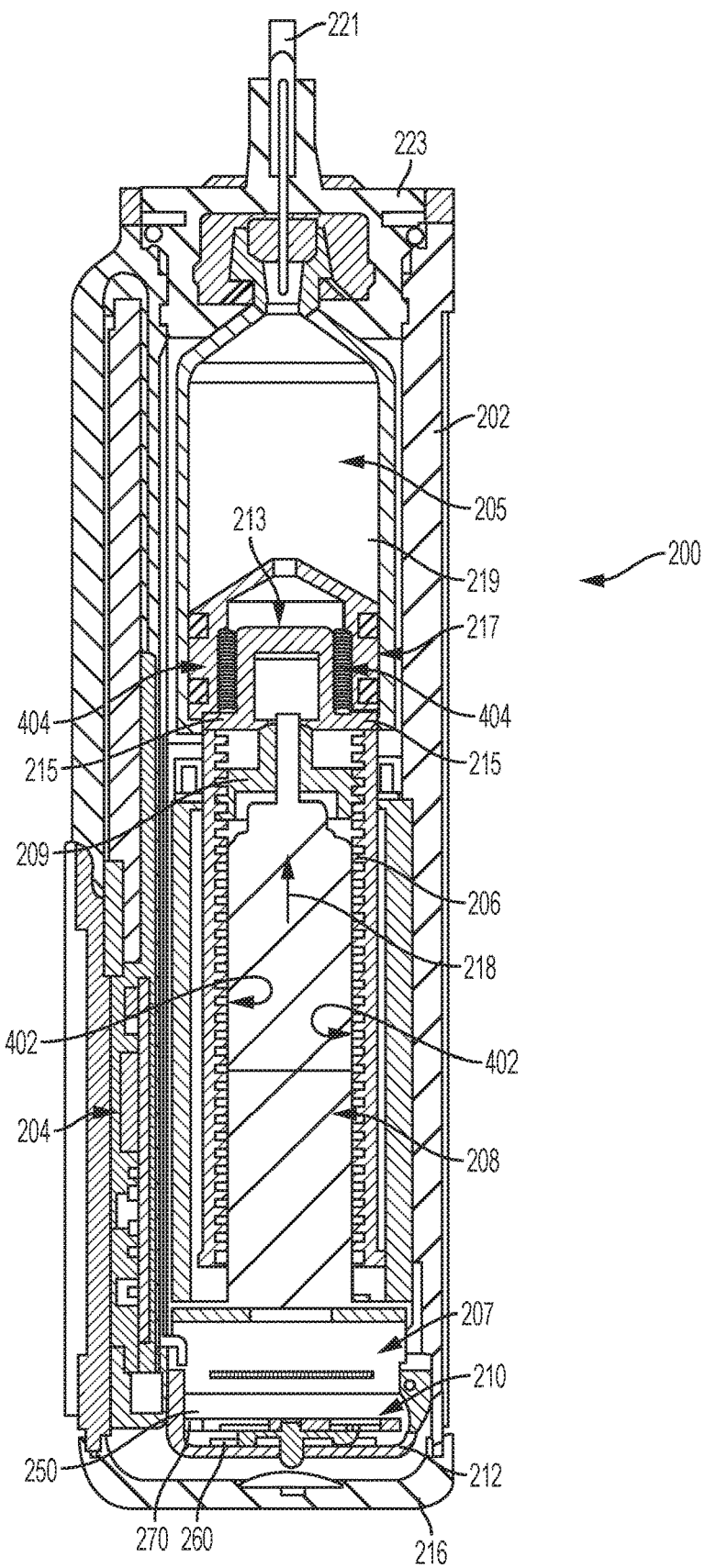
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
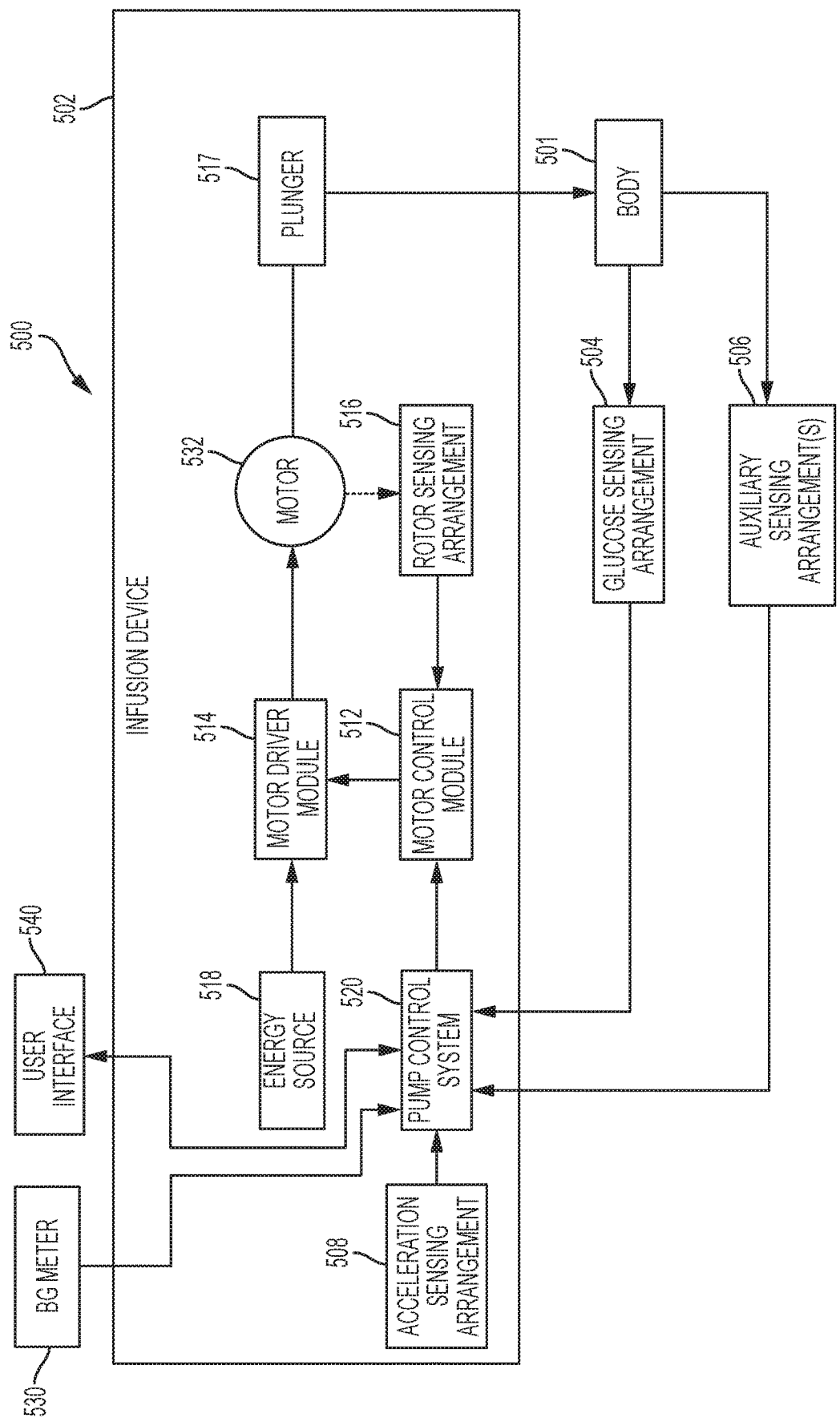
FIG. 5 is a block diagram of an exemplary infusion system suitable for use with a fluid infusion device in one or more embodiments.

FIG. 5 depicts an exemplary embodiment of an infusion system 500 suitable for use with an infusion device 502, such as any one of the infusion devices 102, 200 described above. The infusion system 500 is capable of controlling or otherwise regulating a physiological condition in the body 501 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., sensing arrangement 504) communicatively coupled to the infusion device 502. However, it should be noted that in alternative embodiments, the condition being regulated by the infusion system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the patient's glucose level, which is being regulated in the body 501 of the patient by the infusion system 500.

In exemplary embodiments, the sensing arrangement 504 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 501 of the patient. The output electrical signals are filtered or otherwise processed to obtain a measurement value indicative of the patient's interstitial fluid glucose level. In exemplary embodiments, a blood glucose meter 530, such as a finger stick device, is utilized to directly sense, detect, measure or otherwise quantify the blood glucose in the body 501 of the patient. In this regard, the blood glucose meter 530 outputs or otherwise provides a measured blood glucose value that may be utilized as a reference measurement for calibrating the sensing arrangement 504 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In exemplary embodiments, the infusion system 500 also includes one or more additional sensing arrangements 506, 508 configured to sense, detect, measure or otherwise quantify a characteristic of the body 501 of the patient that is indicative of a condition in the body 501 of the patient. In this regard, in addition to the glucose sensing arrangement 504, one or more auxiliary sensing arrangements 506 may be worn, carried, or otherwise associated with the body 501 of the patient to measure characteristics or conditions of the patient (or the patient's activity) that may influence the patient's glucose levels or insulin sensitivity. For example, a heart rate sensing arrangement 506 could be worn on or otherwise associated with the patient's body 501 to sense, detect, measure or otherwise quantify the patient's heart rate, which, in turn, may be indicative of exercise (and the intensity thereof) that is likely to influence the patient's glucose levels or insulin response in the body 501. In yet another embodiment, another invasive, interstitial, or subcutaneous sensing arrangement 506 may be inserted into the body 501 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 506 could be realized as a standalone component worn by the patient, or alternatively, the auxiliary sensing arrangement(s) 506 may be integrated with the infusion device 502 or the glucose sensing arrangement 504.

The illustrated infusion system 500 also includes an acceleration sensing arrangement 508 (or accelerometer) that may be worn on or otherwise associated with the patient's body 501 to sense, detect, measure or otherwise quantify an acceleration of the patient's body 501, which, in turn, may be indicative of exercise or some other condition in the body 501 that is likely to influence the patient's insulin response. While the acceleration sensing arrangement 508 is depicted as being integrated into the infusion device 502 in FIG. 5, in alternative embodiments, the acceleration sensing arrangement 508 may be integrated with another sensing arrangement 504, 506 on the body 501 of the patient, or the acceleration sensing arrangement 508 may be realized as a separate standalone component that is worn by the patient.

In the illustrated embodiment, the pump control system 520 generally represents the electronics and other components of the infusion device 502 that control operation of the fluid infusion device 502 according to a desired infusion delivery program in a manner that is influenced by the sensed glucose value indicating the current glucose level in the body 501 of the patient. For example, to support a closed-loop operating mode, the pump control system 520 maintains, receives, or otherwise obtains a target or commanded glucose value, and automatically generates or otherwise determines dosage commands for operating an actuation arrangement, such as a motor 532, to displace the plunger 517 and deliver insulin to the body 501 of the patient based on the difference between the sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), insulin delivery limit(s), and/or other glucose threshold value(s) in a data storage element accessible to the pump control system 520. As described in greater detail, in one or more exemplary embodiments, the pump control system 520 automatically adjusts or adapts one or more parameters or other control information used to generate commands for operating the motor 532 in a manner that accounts for a likely change in the patient's glucose level or insulin response resulting from a meal, exercise, or other activity.

Still referring to FIG. 5, the target glucose value and other threshold glucose values utilized by the pump control system 520 may be received from an external component (e.g., CCD 106 and/or computing device 108) or be input by a patient via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the patient to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 532 (e.g., motor assembly 207) that is operable to displace a plunger 517 (e.g., plunger 217) in a reservoir (e.g., reservoir 205) and provide a desired amount of fluid to the body 501 of a patient. In this regard, displacement of the plunger 517 results in the delivery of a fluid, such as insulin, that is capable of influencing the patient's physiological condition to the body 501 of the patient via a fluid delivery path (e.g., via tubing 221 of an infusion set 225). A motor driver module 514 is coupled between an energy source 518 and the motor 532. The motor control module 512 is coupled to the motor driver module 514, and the motor control module 512 generates or otherwise provides command signals that operate the motor driver module 514 to provide current (or power) from the energy source 518 to the motor 532 to displace the plunger 517 in response to receiving, from a pump control system 520, a dosage command indicative of the desired amount of fluid to be delivered.

In exemplary embodiments, the energy source 518 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 518 into alternating electrical signals applied to respective phases of the stator windings of the motor 532 that result in current flowing through the stator windings that generates a stator magnetic field and causes the rotor of the motor 532 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 532 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 532 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 532 to achieve the desired delivery of fluid to the patient.

When the motor control module 512 is operating the motor driver module 514, current flows from the energy source 518 through the stator windings of the motor 532 to produce a stator magnetic field that interacts with the rotor magnetic field. In some embodiments, after the motor control module 512 operates the motor driver module 514 and/or motor 532 to achieve the commanded dosage, the motor control module 512 ceases operating the motor driver module 514 and/or motor 532 until a subsequent dosage command is received. In this regard, the motor driver module 514 and the motor 532 enter an idle state during which the motor driver module 514 effectively disconnects or isolates the stator windings of the motor 532 from the energy source 518. In other words, current does not flow from the energy source 518 through the stator windings of the motor 532 when the motor 532 is idle, and thus, the motor 532 does not consume power from the energy source 518 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 502, while in alternative embodiments, the pump control system 520 may be implemented by a remote computing device that is physically distinct and/or separate from the infusion device 502, such as, for example, the CCD 106 or the computing device 108.

Figure 6:
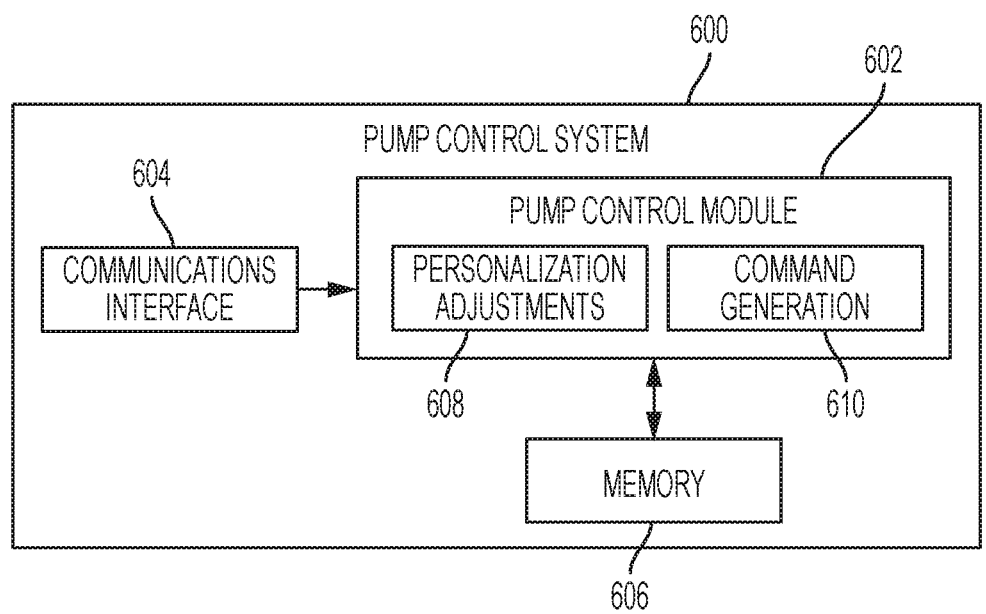
FIG. 6 is a block diagram of an exemplary pump control system suitable for use in the infusion device in the infusion system of FIG. 5 in one or more embodiments.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In various embodiments, the pump control module 602 is also coupled to one or more user interface elements (e.g., user interface 230, 540) for receiving user inputs (e.g., target glucose values or other glucose thresholds) and providing notifications, alerts, or other therapy information to the patient.

The communications interface 604 generally represents the hardware, circuitry, logic, firmware and/or other components of the pump control system 600 that are coupled to the pump control module 602 and configured to support communications between the pump control system 600 and the various sensing arrangements 504, 506, 508. In this regard, the communications interface 604 may include or otherwise be coupled to one or more transceiver modules capable of supporting wireless communications between the pump control system 520, 600 and the sensing arrangement 504, 506, 508. For example, the communications interface 604 may be utilized to receive sensor measurement values or other measurement data from each sensing arrangement 504, 506, 508 in an infusion system 500. In other embodiments, the communications interface 604 may be configured to support wired communications to/from the sensing arrangement(s) 504, 506, 508. In various embodiments, the communications interface 604 may also support communications with another electronic device (e.g., CCD 106 and/or computer 108) in an infusion system (e.g., to upload sensor measurement values to a server or other computing device, receive control information from a server or other computing device, and the like).

The pump control module 602 generally represents the hardware, circuitry, logic, firmware and/or other component of the pump control system 600 that is coupled to the communications interface 604 and configured to determine dosage commands for operating the motor 532 to deliver fluid to the body 501 based on measurement data received from the sensing arrangements 504, 506, 508 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 532 of the infusion device 502 in an autonomous operating mode based at least in part on a current measurement value for a condition in the body 501 of the patient. For example, in a closed-loop operating mode, the command generation application 610 may determine a dosage command for operating the motor 532 to deliver insulin to the body 501 of the patient based at least in part on the current glucose measurement value most recently received from the sensing arrangement 504 to regulate the patient's blood glucose level to a target reference glucose value. Additionally, the command generation application 610 may generate dosage commands for boluses that are manually-initiated or otherwise instructed by a patient via a user interface element.

In exemplary embodiments, the pump control module 602 also implements or otherwise executes a personalization application 608 that is cooperatively configured to interact with the command generation application 610 to support adjusting dosage commands or control information dictating the manner in which dosage commands are generated in a personalized, patient-specific manner. In this regard, in some embodiments, based on correlations between current or recent measurement data and the current operational context relative to historical data associated with the patient, the personalization application 608 may adjust or otherwise modify values for one or more parameters utilized by the command generation application 610 when determining dosage commands, for example, by modifying a parameter value at a register or location in memory 606 referenced by the command generation application 610. In yet other embodiments, the personalization application 608 may predict meals or other events or activities that are likely to be engaged in by the patient and output or otherwise provide an indication of the predicted patient behavior for confirmation or modification by the patient, which, in turn, may then be utilized to adjust the manner in which dosage commands are generated to regulate glucose in a manner that accounts for the patient's behavior in a personalized manner.

Still referring to FIG. 6, depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the applications 608, 610 and perform tasks, operations, functions, and processes described herein.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
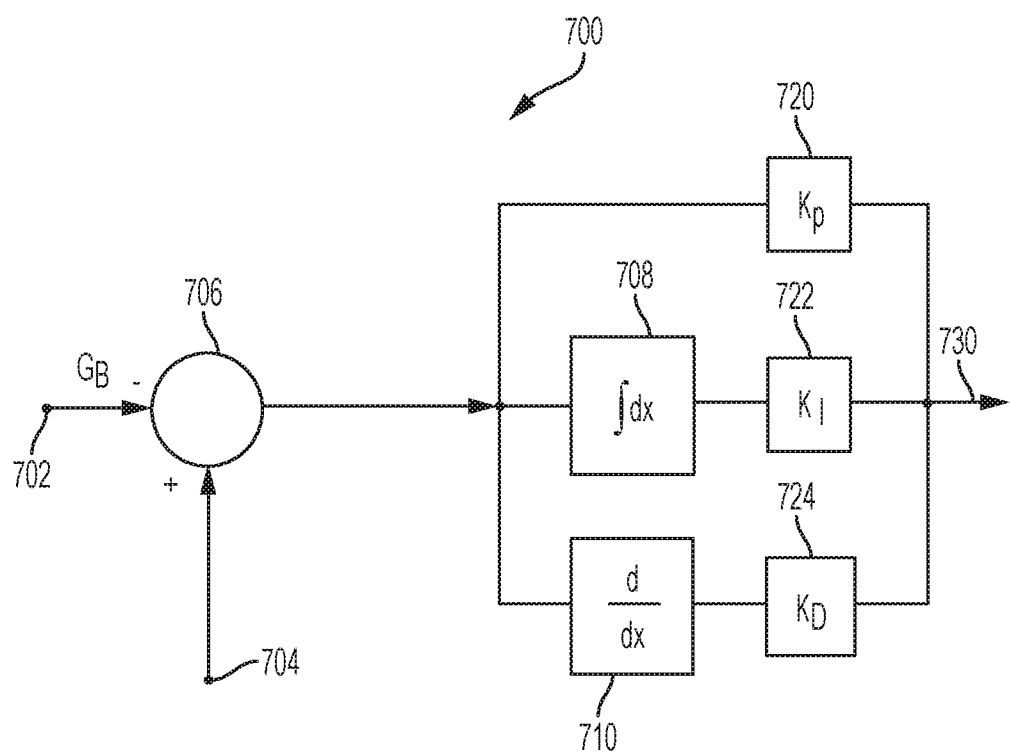
FIG. 7 is a block diagram of a closed-loop control system that may be implemented or otherwise supported by the pump control system in the fluid infusion device of FIGS. 5-6 in one or more exemplary embodiments.

FIG. 7 depicts an exemplary closed-loop control system 700 that may be implemented by a pump control system 520, 600 to provide a closed-loop operating mode that autonomously regulates a condition in the body of a patient to a reference (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 532 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 532 to deliver insulin to the body of the patient to influence the patient's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, KP, to obtain the proportional term. The integral term path includes an integration block 708 that integrates the difference and a gain block 722 that multiplies the integrated difference by an integral gain coefficient, KI, to obtain the integral term. The derivative term path includes a derivative block 710 that determines the derivative of the difference and a gain block 724 that multiplies the derivative of the difference by a derivative gain coefficient, KD, to obtain the derivative term. The proportional term, the integral term, and the derivative term are then added or otherwise combined to obtain a delivery command that is utilized to operate the motor at output 730. Various implementation details pertaining to closed-loop PID control and determining gain coefficients are described in greater detail in U.S. Pat. No. 7,402,153, which is incorporated by reference.

In one or more exemplary embodiments, the PID gain coefficients are patient-specific and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

In one or more exemplary embodiments, one or more parameters of the closed-loop control system 700 are automatically adjusted or adapted in a personalized manner to account for potential changes in the patient's glucose level or insulin sensitivity resulting from meals, exercise, or other events or activities. For example, in one or more embodiments, the target glucose value 702 may be decreased in advance of a predicted meal event to achieve an increase in the insulin infusion rate to effectively pre-bolus a meal, and thereby reduce the likelihood of postprandial hyperglycemia. Additionally or alternatively, the time constant or gain coefficient associated with one or more paths of the closed-loop control system 700 may be adjusted to tune the responsiveness to deviations between the measured glucose value 704 and the target glucose value 702. For example, based on the particular type of meal being consumed or the particular time of day during which the meal is consumed, the time constant associated with the derivative block 710 or derivative term path may be adjusted to make the closed-loop control more or less aggressive in response to an increase in the patient's glucose level based on the patient's historical glycemic response to the particular type of meal.

Figure 8:
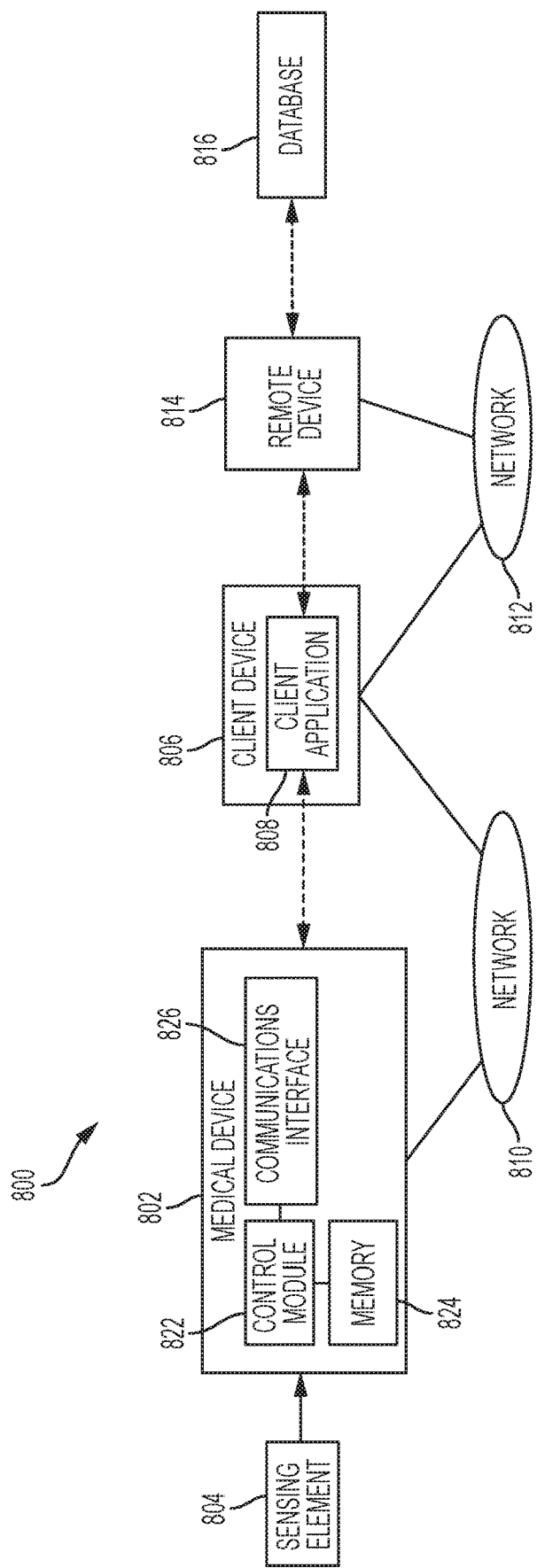
FIG. 8 is a block diagram of an exemplary patient monitoring system.

FIG. 8 depicts an exemplary embodiment of a patient monitoring system 800. The patient monitoring system 800 includes a medical device 802 that is communicatively coupled to a sensing element 804 that is inserted into the body of a patient or otherwise worn by the patient to obtain measurement data indicative of a physiological condition in the body of the patient, such as a sensed glucose level. The medical device 802 is communicatively coupled to a client device 806 via a communications network 810, with the client device 806 being communicatively coupled to a remote device 814 via another communications network 812. In this regard, the client device 806 may function as an intermediary for uploading or otherwise providing measurement data from the medical device 802 to the remote device 814. It should be appreciated that FIG. 8 depicts a simplified representation of a patient monitoring system 800 for purposes of explanation and is not intended to limit the subject matter described herein in any way.

In exemplary embodiments, the client device 806 is realized as a mobile phone, a smartphone, a tablet computer, or other similar mobile electronic device; however, in other embodiments, the client device 806 may be realized as any sort of electronic device capable of communicating with the medical device 802 via network 810, such as a laptop or notebook computer, a desktop computer, or the like. In exemplary embodiments, the network 810 is realized as a Bluetooth network, a ZigBee network, or another suitable personal area network. That said, in other embodiments, the network 810 could be realized as a wireless ad hoc network, a wireless local area network (WLAN), or local area network (LAN). The client device 806 includes or is coupled to a display device, such as a monitor, screen, or another conventional electronic display, capable of graphically presenting data and/or information pertaining to the physiological condition of the patient. The client device 806 also includes or is otherwise associated with a user input device, such as a keyboard, a mouse, a touchscreen, or the like, capable of receiving input data and/or other information from the user of the client device 806.

In exemplary embodiments, a user, such as the patient, the patient's doctor or another healthcare provider, or the like, manipulates the client device 806 to execute a client application 808 that supports communicating with the medical device 802 via the network 810. In this regard, the client application 808 supports establishing a communications session with the medical device 802 on the network 810 and receiving data and/or information from the medical device 802 via the communications session. The medical device 802 may similarly execute or otherwise implement a corresponding application or process that supports establishing the communications session with the client application 808. The client application 808 generally represents a software module or another feature that is generated or otherwise implemented by the client device 806 to support the processes described herein. Accordingly, the client device 806 generally includes a processing system and a data storage element (or memory) capable of storing programming instructions for execution by the processing system, that, when read and executed, cause processing system to create, generate, or otherwise facilitate the client application 808 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 806 and the medical device 802 establish an association (or pairing) with one another over the network 810 to support subsequently establishing a point-to-point or peer-to-peer communications session between the medical device 802 and the client device 806 via the network 810. For example, in accordance with one embodiment, the network 810 is realized as a Bluetooth network, wherein the medical device 802 and the client device 806 are paired with one another (e.g., by obtaining and storing network identification information for one another) by performing a discovery procedure or another suitable pairing procedure. The pairing information obtained during the discovery procedure allows either of the medical device 802 or the client device 806 to initiate the establishment of a secure communications session via the network 810.

In one or more exemplary embodiments, the client application 808 is also configured to store or otherwise maintain an address and/or other identification information for the remote device 814 on the second network 812. In this regard, the second network 812 may be physically and/or logically distinct from the network 810, such as, for example, the Internet, a cellular network, a wide area network (WAN), or the like. The remote device 814 generally represents a server or other computing device configured to receive and analyze or otherwise monitor measurement data, event log data, and potentially other information obtained for the patient associated with the medical device 802. In exemplary embodiments, the remote device 814 is coupled to a database 816 configured to store or otherwise maintain data associated with individual patients. In practice, the remote device 814 may reside at a location that is physically distinct and/or separate from the medical device 802 and the client device 806, such as, for example, at a facility that is owned and/or operated by or otherwise affiliated with a manufacturer of the medical device 802. For purposes of explanation, but without limitation, the remote device 814 may alternatively be referred to herein as a server.

Still referring to FIG. 8, the sensing element 804 generally represents the component of the patient monitoring system 800 that is configured to generate, produce, or otherwise output one or more electrical signals indicative of a physiological condition that is sensed, measured, or otherwise quantified by the sensing element 804. In this regard, the physiological condition of a patient influences a characteristic of the electrical signal output by the sensing element 804, such that the characteristic of the output signal corresponds to or is otherwise correlative to the physiological condition that the sensing element 804 is sensitive to. In exemplary embodiments, the sensing element 804 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 804.

The medical device 802 generally represents the component of the patient monitoring system 800 that is communicatively coupled to the output of the sensing element 804 to receive or otherwise obtain the measurement data samples from the sensing element 804 (e.g., the measured glucose and characteristic impedance values), store or otherwise maintain the measurement data samples, and upload or otherwise transmit the measurement data to the server 814 via the client device 806. In one or more embodiments, the medical device 802 is realized as an infusion device 102, 200, 502 configured to deliver a fluid, such as insulin, to the body of the patient. That said, in other embodiments, the medical device 802 could be a standalone sensing or monitoring device separate and independent from an infusion device (e.g., sensing arrangement 104, 504). It should be noted that although FIG. 8 depicts the medical device 802 and the sensing element 804 as separate components, in practice, the medical device 802 and the sensing element 804 may be integrated or otherwise combined to provide a unitary device that can be worn by the patient.

In exemplary embodiments, the medical device 802 includes a control module 822, a data storage element 824 (or memory), and a communications interface 826. The control module 822 generally represents the hardware, circuitry, logic, firmware and/or other component(s) of the medical device 802 that is coupled to the sensing element 804 to receive the electrical signals output by the sensing element 804 and perform or otherwise support various additional tasks, operations, functions and/or processes described herein. Depending on the embodiment, the control module 822 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 822 includes an analog-to-digital converter (ADC) or another similar sampling arrangement that samples or otherwise converts an output electrical signal received from the sensing element 804 into corresponding digital measurement data value. In other embodiments, the sensing element 804 may incorporate an ADC and output a digital measurement value.

The communications interface 826 generally represents the hardware, circuitry, logic, firmware and/or other components of the medical device 802 that are coupled to the control module 822 for outputting data and/or information from/to the medical device 802 to/from the client device 806. For example, the communications interface 826 may include or otherwise be coupled to one or more transceiver modules capable of supporting wireless communications between the medical device 802 and the client device 806. In exemplary embodiments, the communications interface 826 is realized as a Bluetooth transceiver or adapter configured to support Bluetooth Low Energy (BLE) communications.

In exemplary embodiments, the remote device 814 receives, from the client device 806, measurement data values associated with a particular patient (e.g., sensor glucose measurements, acceleration measurements, and the like) that were obtained using the sensing element 804, and the remote device 814 stores or otherwise maintains the historical measurement data in the database 816 in association with the patient (e.g., using one or more unique patient identifiers). Additionally, the remote device 814 may also receive, from or via the client device 806, meal data or other event log data that may be input or otherwise provided by the patient (e.g., via client application 808) and store or otherwise maintain historical meal data and other historical event or activity data associated with the patient in the database 816. In this regard, the meal data include, for example, a time or timestamp associated with a particular meal event, a meal type or other information indicative of the content or nutritional characteristics of the meal, and an indication of the size associated with the meal. In exemplary embodiments, the remote device 814 also receives historical fluid delivery data corresponding to basal or bolus dosages of fluid delivered to the patient by an infusion device 102, 200, 502. For example, the client application 808 may communicate with an infusion device 102, 200, 502 to obtain insulin delivery dosage amounts and corresponding timestamps from the infusion device 102, 200, 502, and then upload the insulin delivery data to the remote device 814 for storage in association with the particular patient. The remote device 814 may also receive geolocation data and potentially other contextual data associated with a device 802, 806 from the client device 806 and/or client application 808, and store or otherwise maintain the historical operational context data in association with the particular patient. In this regard, one or more of the devices 802, 806 may include a global positioning system (GPS) receiver or similar modules, components or circuitry capable of outputting or otherwise providing data characterizing the geographic location of the respective device 802, 806 in real-time.

The historical patient data may be analyzed by one or more of the remote device 814, the client device 806, and/or the medical device 802 to alter or adjust operation of an infusion device 102, 200, 502 to influence fluid delivery in a personalized manner. For example, the patient's historical meal data and corresponding measurement data or other contextual data may be analyzed to predict a future time when the next meal is likely to be consumed by the patient, the likelihood of a future meal event within a specific time period, the likely size or amount of carbohydrates associated with a future meal, the likely type or nutritional content of the future meal, and/or the like. Moreover, the patient's historical measurement data for postprandial periods following historical meal events may be analyzed to model or otherwise characterize the patient's glycemic response to the predicted size and type of meal for the current context (e.g., time of day, day of week, geolocation, etc.). One or more aspects of the infusion device 102, 200, 502 that control or regulate insulin delivery may then be modified or adjusted to proactively account for the patient's likely meal activity and glycemic response.

In one or more exemplary embodiments, the remote device 814 utilizes machine learning to determine which combination of historical sensor glucose measurement data, historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular event, activity, or metric for a particular patient, and then determines a corresponding equation, function, or model for calculating the value of the parameter of interest based on that set of input variables. Thus, the model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other patients. Additionally, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 814 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

Figure 9:
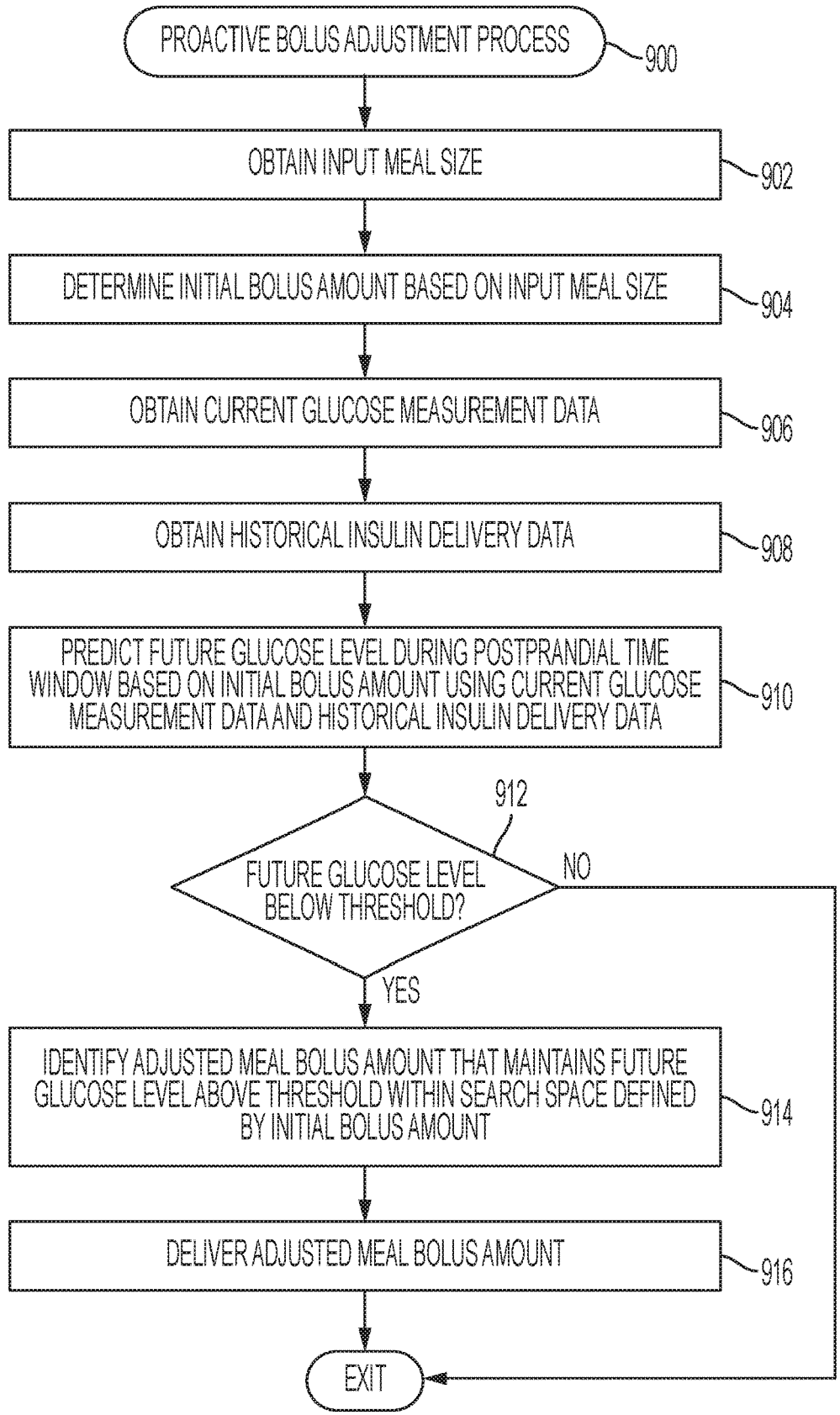
FIG. 9 is a flow diagram of an exemplary proactive bolus adjustment process suitable for use with an infusion device in one or more exemplary embodiments.

FIG. 9 depicts an exemplary proactive bolus adjustment process 900 suitable for implementation by an infusion device (or a control system associated therewith) to adjust a bolus amount to reduce the likelihood of a postprandial hypoglycemic glucose excursion. In this regard, the proactive bolus adjustment process 900 compensates for automated or autonomous insulin deliveries that precede administration of a bolus. The various tasks performed in connection with the proactive bolus adjustment process 900 may be performed by hardware, firmware, software executed by processing circuitry, or any combination thereof. For illustrative purposes, the following description refers to elements mentioned above in connection with FIGS. 1-8. In practice, portions of the proactive bolus adjustment process 900 may be performed by different elements of an infusion system, such as, for example, an infusion device 102, 200, 502, 802, a client computing device 106, 806, a remote computing device 108, 814, and/or a pump control system 520, 600. It should be appreciated that the proactive bolus adjustment process 900 may include any number of additional or alternative tasks, the tasks need not be performed in the illustrated order and/or the tasks may be performed concurrently, and/or the proactive bolus adjustment process 900 may be incorporated into a more comprehensive procedure or process having additional functionality not described in detail herein. Moreover, one or more of the tasks shown and described in the context of FIG. 9 could be omitted from a practical embodiment of the proactive bolus adjustment process 900 as long as the intended overall functionality remains intact.

Referring to FIG. 9 with continued reference to FIGS. 1-8, in exemplary embodiments, the proactive bolus adjustment process 900 is performed in response to a user attempting to initiate a bolus. For example, the patient or another user may manipulate a user interface associated with an infusion device 102, 200, 502, 802 or another device 106, 108, 806 capable of communicating bolus delivery commands to an infusion device 102, 200, 502, 802. In one or more exemplary embodiments, the proactive bolus adjustment process 900 is initiated when the patient interacts with a bolus wizard feature of a particular application 608, 610, 808 used to administer meal boluses. The proactive bolus adjustment process 900 receives or otherwise obtains an indication of a meal size for the meal to be bolused and then calculates or otherwise determines an initial bolus amount based on the input meal size (tasks 902, 904). For example, the client application 808 at the client device 806 may generate or otherwise provide a bolus wizard GUI display that includes selectable GUI elements that allow a user of the client device 806 to input or otherwise provide an estimated amount of carbohydrates to be consumed, a qualitative meal size, a meal content, or other information characterizing the current meal. A corresponding meal bolus amount is calculated or otherwise determined by dividing the amount of carbohydrates associated with the meal by a carbohydrate ratio associated with the patient.

In one or more embodiments, the calculated meal bolus amount also incorporates a correction bolus term when a blood glucose measurement value from a blood glucose meter 530 is obtained or otherwise provided in connection with the meal bolus. For example, the meal bolus (MB) may be calculated using equation $$MB = \frac{Carb}{CR} + \left(\frac{BG - \text{target}}{ISF} - IOB\right),$$

where Carb is the amount of carbohydrates associated with the meal, CR is the carbohydrate ratio associated with the patient, BG is the blood glucose measurement value, target is a target glucose value for the patient, ISF is the insulin sensitivity factor associated with the patient, and IOB is a current amount of insulin on board for the patient. Depending on the embodiment, the insulin sensitivity factor may be set or otherwise defined by a user or calculated based on the patient's total daily insulin does (e.g., by dividing the total daily dose by 1800). Similarly, the carbohydrate ratio may be user-defined or calculated based on the patient's total daily insulin does (e.g., by dividing the total daily dose by 500). The current amount of insulin on board may be calculated or otherwise determined based on historical delivery data for the patient. The target glucose value may be the target value input to the closed-loop control system 700 at 702 or another target glucose value for the patient that may be specified by a user using the bolus wizard.

After determining an initial meal bolus amount based on the input meal size, the proactive bolus adjustment process 900 receives or otherwise obtains the current glucose measurement data and the historical delivery data for the patient and then calculates or otherwise determines predicted values for the patient's future glucose level during a postprandial time window into the future based on the initial meal bolus amount using the current glucose measurement data and the historical insulin delivery data (tasks 906, 908, 910). In this regard, the bolus wizard feature of the application 608, 610, 808 used to administer meal boluses calculates a set of predicted or forecasted glucose measurement values for the patient corresponding to a time period into the future after the patient consumes the meal and administers the input meal bolus amount as a function of the current sensor glucose measurement value, the current sensor glucose measurement derivative or trend, the historical insulin delivery, the amount of carbohydrates associated with the meal, and the amount of insulin for the bolus to be administered. Additionally, the predicted glucose measurement values account for estimated future insulin deliveries that may be automatically or autonomously delivered by the control scheme implemented by the infusion device 102, 200, 502, 802 (e.g., in response to a postprandial rise in the patient's glucose level).

In exemplary embodiments, future glucose values are predicted using a mathematical model of the patient's postprandial glucose response to meals that characterize the glucose response to insulin delivery and corresponding meal consumption by a set of differential equations. These equations may be based on a mass balance between estimated glucose utilization as result of insulin delivery and glucose increase as result of transformation of the meal into blood glucose. The mathematical model may also include specific parameters that enable it to predict the blood glucose at fasting. The mathematical model of the patient's specific meal response may be adjusted using curve fitting, for example, by adjusting the meal absorption rates in the mathematical model to fit the measured historical glucose curve and thereby establish the most proper meal absorption rates.

By way of example, in one embodiment, the mathematical model of the patient's postprandial glucose response is governed by the following set of second order differential equations:

$$\frac{\partial^2 Ip}{\partial t^2} = -\left(\frac{1}{\tau_1} + \frac{1}{\tau_2}\right)\frac{\partial Ip}{\partial t} - \frac{1}{\tau_1 \times \tau_2}Ip + K_1 I_{in}, \quad \text{Equation (1)}$$

$$\frac{\partial^2 G_{meal}}{\partial t^2} = -\frac{2}{\tau_5}\frac{\partial G_{meal}}{\partial t} - \frac{1}{\tau_5^2}G_{meal} + K_2 CARB, \text{ and} \quad \text{Equation (2)}$$

$$\frac{\partial^2 G_{sc}}{\partial t^2} = -\left(\frac{1}{\tau_3} + \frac{1}{\tau_4}\right)\frac{\partial G_{sc}}{\partial t} - \frac{1}{\tau_3 \times \tau_4}G_{sc} - K_I I_p + K_M G_{meal}, \quad \text{Equation (3)}$$

where Ip is the plasma insulin concentration (in units per deciliter or U/dL) which includes or incorporates both basal and bolus insulin deliveries, $K_1$ is a constant (one per deciliter per minute or 1/min/dL), $I_{in}$ is the insulin rate of delivery into the subcutaneous tissue (in units per minute or U/min), $G_{sc}$ represents the patient's glucose level (mg/dL), $G_{meal}$ is the concentration of glucose that originated from carbohydrates consumed by the patient (mg/dL), $K_2$ is a constant (mg per carbohydrates per square minute per deciliter or mg/carbs/min²/dL), CARB is the amount of carbohydrates consumed by the patient, $\tau_1$ and $\tau_2$ are plasma insulin concentration time constants, $\tau_3$ and $\tau_4$ are glucose concentration time constants, $\tau_5$ is a carbohydrate transformation into milligram of glucose time constant, $K_M$ is conversion constant (one per square minutes or 1/min²), and $K_I$ is conversion constant (mg per units per square minutes or mg/U/min²). The time constants ($\tau_1$-$\tau_5$), glucose conversion constant ($K_M$) and insulin conversion constant ($K_I$) may be determined based on historical glucose measurement data, historical insulin delivery data, historical meal data and/or other historical event log data which may be maintained by one or more components 802, 806, 814, 816 of a patient monitoring system 800. In one embodiment, the carbohydrate transformation into milligram of glucose time constant ($\tau_5$) and the and insulin conversion constant ($K_I$) are patient-specific and determined based on historical data associated with the patient of interest, while the remaining constants are determined on a population basis across a number of different patients. For example, in one embodiment, the patient's insulin conversion constant ($K_I$) may be determined based on the patient's total daily dose of insulin over a preceding period of time (e.g., as a function of the median total daily dose for the preceding 6 days).

To calculate future glucose values for the patient, the differential equations are initialized by calculating the initial plasma insulin (Ip) and its time derivative $$\left(\frac{\partial Ip}{\partial t}\right)$$

using Equation (1) based on the historical insulin delivery preceding the current instant in time and calculating the initial meal compartment glucose concentration ($G_{meal}$) and its time derivative $$\left(\frac{\partial G_{meal}}{\partial t}\right)$$

using Equation (2) based on the historical meal data preceding the current instant in time. The initial value for the patient's glucose level ($G_{sc}$) may be set to the value of the current or most recent sensor glucose measurement sample obtained by a sensing arrangement 104, 504, 804, and the initial value for the time derivative of the patient's glucose $$\left(\frac{\partial G_{sc}}{\partial t}\right)$$

may be calculated based on the values for the current and preceding sensor glucose measurement samples. In the absence of sensor glucose measurement data, the initial conditions for the patient's glucose level ($G_{sc}$) and its time derivative $$\left(\frac{\partial G_{sc}}{\partial t}\right)$$

may be calculated based on historical blood glucose measurements and/or other historical glucose measurements using Equation (3).

After determining initial values for the patient's plasma insulin (Ip), plasma insulin time derivative $$\left(\frac{\partial Ip}{\partial t}\right),$$

the patient's meal compartment glucose concentration ($G_{meal}$), the meal compartment glucose time derivative $$\left(\frac{\partial G_{meal}}{\partial t}\right),$$

the patient's glucose level, and the patient's glucose time derivative $$\left(\frac{\partial G_{sc}}{\partial t}\right),$$

the CARB variable in Equation (2) is set to the amount of carbohydrates associated with the meal to be bolused and the insulin rate of delivery variable ($I_{in}$) in Equation (1) is set to the initial meal bolus amount. The set of differential equations are then utilized to calculate predicted values for the patient's glucose level ($G_{cs}$) at different times in the future from the initialized conditions. For example, predicted values for the patient's glucose level ($G_{sc}$) may be calculated at regular intervals into the future (e.g., every five minutes) for a duration of time corresponding to a postprandial analysis time window. For purpose of predicting the patient's future glucose level, the CARE term in Equation (2) may be set to zero for subsequent instances in time. Additionally, the future insulin delivery rate ($I_{in}$) in Equation (1) for subsequent instances in time may be set to a constant rate (e.g., the patient's basal rate). In other embodiments, the future insulin delivery rate may be dynamically determined based on a current or preceding glucose value ($G_{sc}$) and the control scheme implemented by the infusion device 102, 200, 502, 802 to effectively simulate the automated or autonomous response to a postprandial rise in the patient's glucose level (e.g., to estimate the response of the closed-loop control system 700).

Still referring to FIG. 9, the proactive bolus adjustment process 900 verifies or otherwise determines whether the predicted glucose values for the patient during the postprandial time window into the future are maintained above a threshold value (task 912). In this regard, the proactive bolus adjustment process 900 detects or otherwise identifies when at least one of the predicted glucose values for the patient during the postprandial analysis time window falls below a threshold value. For example, in one embodiment, the proactive bolus adjustment process 900 identifies when a predicted future glucose value for the patient resulting from the combination of the currently estimated amount of carbohydrates to be consumed and corresponding meal bolus falls below a threshold value of 50 mg/dL within the next 4 hours. That said, it should be noted that the glucose threshold value and/or the duration of the postprandial analysis time window may vary, and the subject matter described herein is not limited to any particular threshold value and/or duration for the postprandial analysis period.

When the predicted future glucose level for the patient falls below the threshold during the postprandial analysis time period, the proactive bolus adjustment process 900 identifies an adjusted bolus amount that maintains the predicted future glucose level for the patient above the threshold during the postprandial analysis time period (task 914). In this regard, the proactive bolus adjustment process 900 identifies an adjusted bolus amount that when used as the insulin rate of delivery variable ($I_{in}$) in Equation (1) with the initialized conditions described above that results in each of the predicted future values for the patient's glucose level ($G_{sc}$) during the postprandial analysis time window being maintained above the threshold value. As described in greater detail below in the context of FIG. 11, in exemplary embodiments, the proactive bolus adjustment process 900 identifies the maximum value for the initial insulin rate of delivery variable ($I_{in}$) in Equation (1) that maintains the predicted future values for the patient's glucose level ($G_{sc}$) above the threshold value during the postprandial analysis time window from within the search space defined by the initial bolus amount determined based on the input meal size. Thus, the adjusted bolus amount maximizes the amount of insulin to be delivered by the meal bolus while accounting for preceding and/or future insulin deliveries and reducing the likelihood of a postprandial hypoglycemic event by maintaining the predicted future glucose level above the threshold given the combination of the current estimated amount of carbohydrates to be consumed, the patient's current glucose level and its current time derivative, and the patient's current plasma insulin concentration resulting from preceding insulin deliveries.

Figure 10:
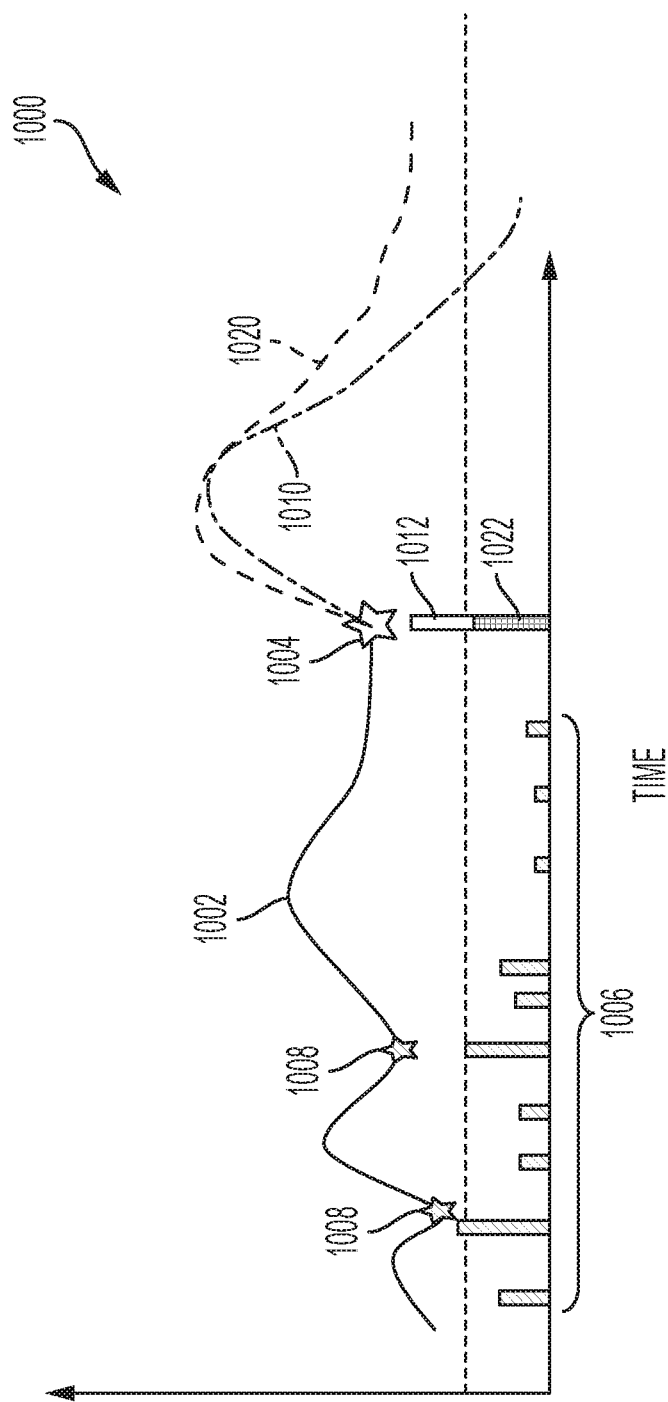
FIG. 10 is a graph depicting predicted future glucose levels for different bolus amounts in connection with the proactive bolus adjustment process of FIG. 9.

FIG. 10 depicts an exemplary graph 1000 of predicted glucose levels for the patient for different meal bolus amounts for a current amount of carbohydrates to be consumed calculated based on the patient's current glucose level and its current time derivative and the patient's current plasma insulin concentration resulting from preceding insulin deliveries. The graph 1000 depicts a graphical representation 1002 of the patient's sensor glucose measurements preceding the current meal event 1004 to be bolused for, along with bars 1006 representing the amounts and timings associated with historical insulin deliveries and indicia 1008 of the timing of preceding meal events. Additionally, the graph 1000 depicts a graphical representation 1010 of the patient's predicted future glucose levels for a postprandial time period after the current meal event 1004 that are calculated or otherwise determined based on an initial meal bolus amount (represented by bar 1012). As described above, the initial meal bolus amount 1012 is calculated or otherwise determined using a carbohydrate ratio associated with the patient based on an estimated amount of carbohydrates associated with the meal event 1004 (e.g., task 904). To calculate the predicted future glucose values 1010, the historical insulin deliveries 1006, historical meal events 1008, and the current and preceding sensor glucose measurements 1002 are utilized to initialize the mathematical models for the patient's condition in conjunction with the estimated amount of carbohydrates associated with the meal event 1004 and the initial meal bolus amount 1012. When the predicted future glucose value 1010 falls below a threshold 1014 (e.g., task 912), the proactive bolus process 900 identifies an adjusted bolus amount (indicated by bar 1022) that results in predicted future glucose values 1020 for the patient being maintained above the threshold 1014 during the postprandial analysis time window.

Referring again to FIG. 9, in one or more embodiments, after identifying the adjusted bolus amount, the proactive bolus adjustment process 900 initiates or otherwise facilitates delivery of the adjusted bolus amount in lieu of the initial bolus amount determined based on the input meal size (task 916). In some embodiments, the adjusted meal bolus dosage may be automatically administered in lieu of the initial bolus amount; however, in other embodiments, a notification of the calculated meal bolus dosage may be generated or otherwise provided on a GUI display for review, modification, and/or confirmation by the patient. For example, in one or more embodiments, the proactive bolus adjustment process 900 may display the adjusted bolus amount on the bolus wizard GUI display or otherwise provide a notification of the adjusted bolus amount to the patient along with a corresponding GUI element that is selectable by the patient to confirm the adjusted bolus amount and initiate delivery. Such a GUI display may also include indication of the estimated carbohydrate ratio and estimated carbohydrate amount for review, modification, and/or confirmation. In this regard, some embodiments may allow the patient to modify one or more of the carbohydrate ratio, the carbohydrate amount, or the bolus dosage amount. In response to modification of the carbohydrate ratio or the carbohydrate amount, proactive bolus adjustment process 900 may repeat the analysis based on the meal bolus amount resulting from the adjusted carbohydrate ratio and/or amount (e.g., tasks 904, 906, 908, 910 and 912). Once the adjusted bolus amount is confirmed, the command generation application 610 may then be commanded, signaled, or otherwise instructed to operate the motor 532 of the infusion device 502 to deliver the adjusted bolus dosage of insulin.

Figure 11:
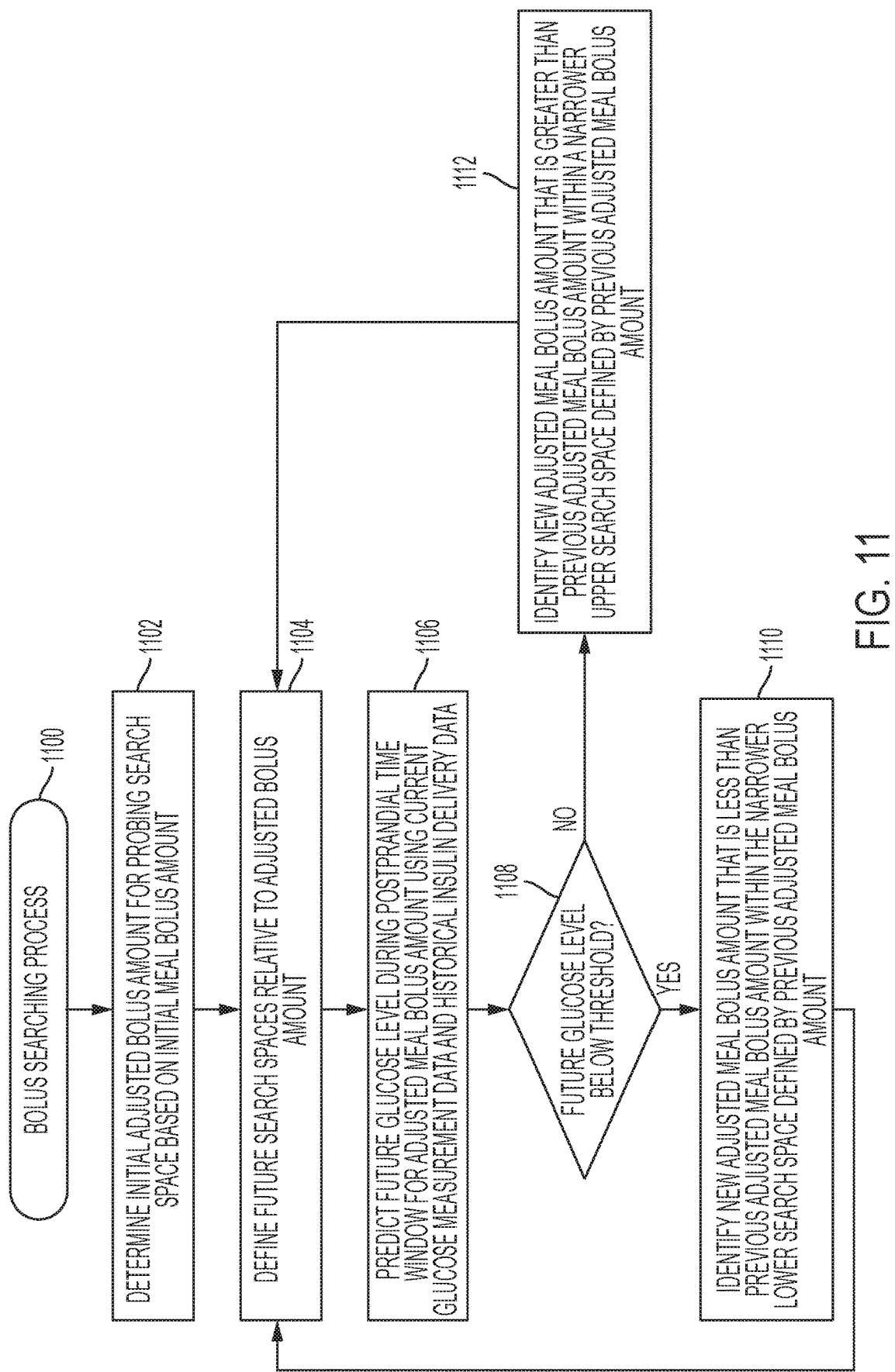
FIG. 11 is a flow diagram of an exemplary bolus search process suitable for use with an infusion device in one or more exemplary embodiments.

FIG. 11 depicts an exemplary bolus search process 1100 suitable for implementation in connection with the proactive bolus adjustment process 900 (e.g., task 914) to identify an adjusted bolus amount that maximizes the bolus dosage amount while maintaining predicted future glucose values above a threshold value during a subsequent time period. The various tasks performed in connection with the bolus search process 1100 may be performed by hardware, firmware, software executed by processing circuitry, or any combination thereof. For illustrative purposes, the following description refers to elements mentioned above in connection with FIGS. 1-10. It should be appreciated that the bolus search process 1100 may include any number of additional or alternative tasks, the tasks need not be performed in the illustrated order and/or the tasks may be performed concurrently, and/or the bolus search process 1100 may be incorporated into a more comprehensive procedure or process having additional functionality not described in detail herein. Moreover, one or more of the tasks shown and described in the context of FIG. 11 could be omitted from a practical embodiment of the bolus search process 1100 as long as the intended overall functionality remains intact.

In exemplary embodiments, the bolus search process 1100 performs a golden section search (or golden ratio search) or other Fibonacci search technique that attempts to arrive at a maximum bolus dosage amount that maintains predicted future glucose values above a threshold value during a subsequent time period. The bolus search process 1100 identifies or otherwise determines an initial adjusted bolus amount to be used to probe or text for use in lieu of the initial meal bolus amount that was originally determined (e.g., at task 904) using the input meal size and carbohydrate ratio (task 1102). In this regard, the bolus search process 1100 identifies the initial adjusted bolus amount within a search space defined by a bolus of zero as a lower limit and an upper limit equal to the initial meal bolus amount ($b_{meal}$). In exemplary embodiments, the golden ratio is utilized to identify the initial adjusted bolus amount as a fraction of the initial meal bolus amount corresponding to the golden ratio by multiplying the initial meal bolus amount by 0.618. That said, the subject matter described herein is not intended to be limited to any particular manner for dividing the search space. The bolus search process 1100 also utilizes the initial adjusted bolus amount to define or otherwise determine search spaces for subsequent analysis (task 1104). For example, an upper search space may be defined relative to the initial adjusted bolus amount as being bounded by the initial adjusted bolus amount as its lower limit and the initial meal bolus amount as its upper limit (e.g., [$0.618b_{meal}$, $b_{meal}$]), while a lower search space may be bounded by the initial adjusted bolus amount as its upper limit and a bolus dosage of zero as its lower limit (e.g., [$0, 0.618b_{meal}$]).

The bolus search process 1100 continues by calculating or otherwise determining predicted values for the patient's future glucose level during a postprandial time window into the future based on the initial adjusted bolus amount using the current glucose measurement data and the historical insulin delivery data (task 1106) in a similar manner as described above (e.g., task 910). In this regard, the mathematical model of the patient's postprandial glucose response is initialized with the initial adjusted bolus amount (e.g., $0.618b_{meal}$) in lieu of the initial meal bolus amount. In a similar manner as described above (e.g., task 912), the bolus search process 1100 verifies or otherwise determines whether or not the predicted glucose values for the patient during the postprandial time window into the future are maintained above a threshold value when the initial adjusted bolus amount is utilized before selecting a new search space for analysis based on the outcome (tasks 1108, 1110, 1112). In this manner, the initial adjusted bolus amount is used to probe the initial search space and identify which narrower search space defined relative to the initial adjusted bolus amount should be utilized for determining subsequent bolus amounts for further probing or testing, which, in turn, progressively or iteratively narrows the search space and converges towards a maximum or optimal bolus dosage that maintains the predicted glucose values above the hypoglycemic threshold for the duration of the postprandial time window.

When one or more predicted glucose values for the patient during the postprandial analysis time period are below the threshold, the bolus search process 1100 utilizes the lower search space defined by the adjusted bolus amount to identify or otherwise determine an updated adjusted bolus amount (task 1110) and redefine subsequent search spaces (task 1104). For example, the bolus search process 1100 may identify an updated adjusted bolus amount within the lower search space by dividing the lower search space according to the golden ratio, that is, by multiplying the initial adjusted bolus amount by 0.618 to obtain an updated bolus amount equal to 0.382 times the initial meal bolus amount. The bolus search process 1100 then defines a lower search space relative to the updated bolus amount having a lower limit defined by the previous lower limit for the search space used to identify the updated bolus amount (e.g., [$0, 0.382b_{meal}$]) and an upper search space relative to the updated bolus amount having an upper limit defined by the previous upper limit for the search space used to identify the updated bolus amount (e.g., [$0.382b_{meal}$, $0.618b_{meal}$]). Thereafter, the bolus search process 1100 continues by calculating or otherwise determining predicted values for the patient's future glucose level during a postprandial time window into the future based on the updated adjusted bolus by initializing the mathematical model of the patient's postprandial glucose response using the updated adjusted bolus amount (e.g., $0.382b_{meal}$) (task 1106). Again, the bolus search process 1100 verifies or otherwise determines whether the predicted glucose values for the patient during the postprandial time window into the future are maintained above a threshold value, and then based on the outcome of that determination, selects one of the search spaces defined relative to the updated adjusted bolus amount (e.g., the upper search space of [$0.382b_{meal}$, $0.618b_{meal}$] if the predicted glucose values are maintained above the threshold or the lower search space of [$0, 0.382b_{meal}$] otherwise) for further analysis (tasks 1108, 1110, 1112). In this regard, if the predicted glucose values are maintained above the threshold when the bolus amount of $0.382b_{meal}$ is used, the golden ratio may be utilized to divide the upper search space to obtain an updated bolus amount of $0.528b_{meal}$ and updated search spaces of [$0.382b_{meal}$, $0.528b_{meal}$] and [$0.528b_{meal}$, $0.618b_{meal}$] for further analysis (tasks 1104 and 1112).

Similarly, when the initial adjusted bolus amount of $0.618b_{meal}$ maintains the predicted glucose values for the patient during the postprandial analysis time period above the threshold, the bolus search process 1100 divides the upper search space defined by the adjusted bolus amount to identify or otherwise determine an updated adjusted bolus amount (task 1112). For example, the bolus search process 1100 may divide the upper search space of [$0.618b_{meal}$, $b_{meal}$] according to the golden ratio to obtain an updated bolus amount of $0.854b_{meal}$. The bolus search process 1100 then defines a lower search space relative to the updated bolus amount having a lower limit defined by the previous lower limit for the search space used to identify the updated bolus amount (e.g., [$0.618b_{meal}$, $0.854b_{meal}$]) and an upper search space relative to the updated bolus amount having an upper limit defined by the previous upper limit for the search space used to identify the updated bolus amount (e.g.,

[0.854$b_{meal}$, $b_{meal}$]) (task 1104). Thereafter, the bolus search process 1100 continues by calculating or otherwise determining predicted values for the patient's future glucose level using the updated adjusted bolus by initializing the mathematical model of the patient's postprandial glucose response using the updated adjusted bolus amount of 0.854$b_{meal}$ (task 1106). If the predicted glucose values for the patient during the postprandial time window into the future are maintained above the threshold value when the bolus amount of 0.854$b_{meal}$ is used, the golden ratio may be utilized to further divide the upper search space to obtain an updated bolus amount of 0.944$b_{meal}$ and updated search spaces of [0.854$b_{meal}$, 0.944$b_{meal}$] and [0.944$b_{meal}$, $b_{meal}$] for further analysis. Conversely, if the bolus amount of 0.854$b_{meal}$ results in a predicted glucose value below the threshold during the postprandial time period, the golden ratio may be utilized to further divide the lower search space to obtain an updated bolus amount of 0.764$b_{meal}$ and updated search spaces of [0.618$b_{meal}$, 0.764$b_{meal}$] and [0.764$b_{meal}$, 0.854$b_{meal}$] for further analysis.

In exemplary embodiments, the bolus search process 1100 repeats the loop defined by tasks 1104, 1106, 1108, 1110 and 1112 for a predefined number of times before reaching a termination condition and selecting the final adjusted bolus amount as the adjusted bolus amount to be utilized in lieu of the initial meal bolus amount. For example, the bolus search process 1100 may be limited to a threshold number of iterations (e.g., 20 iterations), where after the threshold number of divisions of the search space have been performed, the most recent adjusted bolus amount that maintained future glucose levels above the threshold is selected or otherwise identified for use by the proactive bolus adjustment process 900. That said, in other embodiments, the bolus search process 1100 may repeat the loop defined by tasks 1104, 1106, 1108, 1110 and 1112 until achieving a desired level of convergence on an optimal solution, for example, until the resulting search spaces are less than some fraction of the original search space or less than some amount of insulin (e.g., when the sum of the resulting search spaces is less than 0.1 Units), before then selecting the most recent adjusted bolus amount that maintained future glucose levels above the threshold. In the absence of identifying an adjusted bolus amount that maintains future glucose levels above the threshold, the bolus search process 1100 may set the final adjusted bolus amount to zero.

It should be appreciated that by virtue of the bolus search process 1100 iteratively dividing search spaces and selecting corresponding adjusted bolus amounts within those progressively narrowing search spaces, the bolus search process 1100 attempts to identify the maximum bolus dosage amount that still maintains predicted glucose values above the threshold, to thereby achieve an adjusted meal bolus amount that best approximates the meal bolus amount that would otherwise have been administered based on the patient's carbohydrate ratio while also reducing the likelihood of a postprandial hypoglycemic event without requiring suspension or other modification to any automated or autonomous operating modes being utilized or implemented by an infusion device concurrently to the meal bolus. It should also be noted that although the subject matter is primarily described herein in the context of a meal, the subject matter is not necessarily limited to meal boluses and may be extended to boluses that accompany any other sort of event indication that could raise glucose levels or otherwise affect the physiological condition of a patient (e.g., exercise, acute stress, etc.).

It should be noted that the subject matter described herein is not limited to a golden ratio-based search or a Fibonacci search, and any number of suitable alternative searching or optimization methods (e.g., gradient-based search methods, brute force search methods, Newton's method, quadratic optimization, simulated annealing, genetic algorithm, and the like) may be used to identify or otherwise approximate an optimal value for the bolus input variable that maintains future glucose levels above a threshold for the duration of a desired postprandial time period. For example, a linear search method may be employed to divide the search space into a number of different values and progress from the highest value towards the lowest to identify the highest of the values that maintains the future glucose levels above the threshold. As another example, rather than using the golden-ratio, the search space may be progressively divided in half or some other fraction similar to the Fibonacci method until arriving at an approximate optimal value. As yet another example, a cost function approach may be utilized. In this regard, the cost function may have a higher price for predicted glucose values below the threshold and lighter price for being above the predefined threshold. The search may then attempt to identify an optimal bolus value that results in postprandial predicted glucose values that approach the threshold (e.g., using a Newton-Raphson type of search to converge to an optimal bolus amount). That said, a golden ratio-based search is a computationally efficient way to identify an approximate optimal value.

For the sake of brevity, conventional techniques related to glucose sensing and/or monitoring, bolusing, closed-loop glucose control, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating an infusion device capable of delivering fluid influencing a physiological condition to a patient, the method comprising:

obtaining, by a control system associated with the infusion device, an event indication;

determining, by the control system, an initial bolus amount based on the event indication;

determining, by the control system, predicted values for the physiological condition of the patient during a time window based at least in part on the initial bolus amount; and when the predicted values violate a threshold during the time window:

identifying, by the control system, an adjusted bolus amount within a search space defined by the initial bolus amount that results in the predicted values for the physiological condition satisfying the threshold during the time window; and operating, by the control system, an actuation arrangement of the infusion device to deliver the adjusted bolus amount of the fluid to the patient.

2. The method of claim 1, wherein identifying the adjusted bolus amount comprises maximizing the adjusted bolus amount within the search space, wherein the adjusted bolus amount is less than the initial bolus amount.

3. The method of claim 1, wherein identifying the adjusted bolus amount comprises progressively reducing the search space to arrive at the adjusted bolus amount.

4. The method of claim 1, wherein progressively reducing the search space comprises progressively reducing the search space to maximize the adjusted bolus amount within the search space using one or more intermediate adjusted bolus amounts until reaching a termination condition, wherein progressively reducing the search space comprises, for each of one or more intermediate bolus amounts within the search space:

determining a respective initial condition for the patient at a time corresponding to the event indication based at least in part on the respective intermediate bolus amount;

determining respective predicted values for the physiological condition of the patient during the time window based at least in part on a carbohydrate amount corresponding to a meal at the time corresponding to the event indication and the respective initial condition; and identifying a subsequent intermediate bolus amount of the one or more intermediate bolus amounts between the respective intermediate bolus amount and a preceding bolus amount based on a relationship between the respective predicted values for the physiological condition of the patient and the threshold.

5. The method of claim 1, wherein identifying the adjusted bolus amount comprises searching the search space using a golden ratio search for a maximum bolus dosage that maintains the predicted values for the physiological condition above the threshold during the time window.

6. The method of claim 1, further comprising determining future delivery of the fluid for the patient, resulting in future delivery data, wherein determining the predicted values for the physiological condition comprises determining the predicted values for the physiological condition based at least in part on the future delivery data.

7. The method of claim 6, wherein determining the future delivery data comprises identifying a fixed rate of automated delivery of the fluid implemented by an autonomous operating mode of the infusion device.

8. The method of claim 6, wherein determining the future delivery data comprises estimating a variable rate of automated delivery of the fluid implemented by an autonomous operating mode of the infusion device.

9. The method of claim 8, wherein estimating the variable rate comprises simulating operation of a closed-loop control system during the time window.

10. The method of claim 6, further comprising:

obtaining historical delivery data for the patient; and determining an initial condition for the patient at a time corresponding to the event indication based at least in part on the historical delivery data, wherein determining the predicted values for the physiological condition comprises determining the predicted values for the physiological condition based at least in part on the future delivery data and the initial condition for the patient.

11. The method of claim 10, the fluid comprising insulin and the event indication comprising a meal indication, wherein determining the initial condition for the patient comprises determining an initial plasma insulin concentration for the patient at the time corresponding to the meal indication based at least in part on the initial bolus amount and the historical delivery data; and determining the predicted values for the physiological condition comprises determining the predicted values for a glucose level of the patient during the time window based at least in part on the future delivery data, a carbohydrate amount corresponding to the meal indication at the time corresponding to the meal indication, and the initial plasma insulin concentration at the time corresponding to the meal indication.

12. The method of claim 11, wherein identifying the adjusted bolus amount comprises progressively reducing the search space to maximize the adjusted bolus amount within the search space using one or more intermediate adjusted bolus amounts, wherein progressively reducing the search space comprises, for each of the one or more intermediate adjusted bolus amounts:

determining a respective initial plasma insulin concentration for the patient at the time corresponding to the meal indication based at least in part on the respective intermediate adjusted bolus amount and the historical delivery data;

determining respective predicted values for the glucose level of the patient during the time window based at least in part on the future delivery data, the carbohydrate amount corresponding to the meal indication at the time corresponding to the meal indication, the respective initial plasma insulin concentration at the time corresponding to the meal indication; and identifying a subsequent intermediate adjusted bolus amount of the one or more intermediate adjusted bolus amounts based on a relationship between the respective predicted values for the glucose level of the patient and the threshold.

13. The method of claim 1, further comprising:

obtaining historical insulin delivery data for the patient; and determining an initial plasma insulin concentration for the patient at a time corresponding to the event indication based at least in part on the historical insulin delivery data, wherein determining the predicted values for the physiological condition comprises determining the predicted values for a glucose level of the patient during the time window based at least in part on the initial plasma insulin concentration, a carbohydrate amount corresponding to a meal at the time corresponding to the event indication, and estimated future insulin delivery data.

14. The method of claim 13, further comprising obtaining glucose measurement data for the patient, wherein determining the predicted values comprises determining the predicted values for the glucose level of the patient based at least in part on the initial plasma insulin concentration, the glucose measurement data, the carbohydrate amount, and the estimated future insulin delivery data.

15. The method of claim 1, further comprising:
obtaining glucose measurement data for the patient;
obtaining historical insulin delivery data for the patient; and
determining an initial condition for the patient at a time corresponding to the event indication based at least in part on the historical insulin delivery data, the glucose measurement data, the initial bolus amount of insulin at the time corresponding to the event indication, and a carbohydrate amount corresponding to a meal at the time corresponding to the event indication, wherein determining the predicted values for the physiological condition comprises determining the predicted values for a glucose level for the patient during the time window based at least in part on the initial condition for the patient and future insulin delivery data.

* * * * *